United States Patent [19]

Hedegaard et al.

[11] Patent Number: 5,182,081
[45] Date of Patent: Jan. 26, 1993

[54] PRODUCT TO BE USED IN OCCLUSIVE EPICUTANEOUS TESTING FOR THE PURPOSE OF DEMONSTRATING CONTACT ALLERGY TO FORMALDEHYDE

[75] Inventors: Kurt Hedegaard, Hørsholm; Sten Albrectsen, Holte; Jens Hansen, Allerød, all of Denmark

[73] Assignee: Kabi Pharmacia AB, Uppsala, Sweden

[21] Appl. No.: 460,197

[22] PCT Filed: Jun. 12, 1989

[86] PCT No.: PCT/SE89/00330
§ 371 Date: Feb. 1, 1990
§ 102(e) Date: Feb. 1, 1990

[87] PCT Pub. No.: WO90/00064
PCT Pub. Date: Jan. 11, 1990

[30] Foreign Application Priority Data
Jun. 28, 1988 [SE] Sweden .................... 8802403-9

[51] Int. Cl.$^5$ .................... A61B 5/00; G01N 31/22
[52] U.S. Cl. .................... 422/56; 128/743
[58] Field of Search .................... 422/56; 128/743

[56] References Cited

U.S. PATENT DOCUMENTS

| 2,304,817 | 12/1942 | Grozin | 128/743 |
| 4,450,844 | 5/1984 | Quisno | 128/743 |
| 4,836,217 | 6/1989 | Fischer | 128/743 |
| 4,887,611 | 12/1989 | Rüdiger et al. | 128/743 |

FOREIGN PATENT DOCUMENTS

0252044 7/1988 European Pat. Off.

OTHER PUBLICATIONS

Contact Dermatitis 1986: 15:218-222—Contact Allergy to Preservatives-II Anton C. DeGroot et al.
J. Am. Acad. Derm. 21 (1989) 838-840 Hansen et al.

Primary Examiner—Jill A. Johnston
Assistant Examiner—Arlen Soderquist
Attorney, Agent, or Firm—Fred Philpitt

[57] ABSTRACT

A test strip having at least one patch thereon and intended for use in occlusive epicutaneous testing in order to detect contact allergy to formaldehyde. The characteristic feature is that on at least one of the patches the test substance is a reversible N-formaldehyde derivative of succinimide which is formulated in a dry buffered vehicle.

3 Claims, No Drawings

PRODUCT TO BE USED IN OCCLUSIVE EPICUTANEOUS TESTING FOR THE PURPOSE OF DEMONSTRATING CONTACT ALLERGY TO FORMALDEHYDE

TECHNICAL BACKGROUND

The popular, English language derived name for occlusive epicutaneous testing is "patch test".

This term "patch test" reflects the fact that from the end of the 19th century onwards patches of fabric or paper were employed which were soaked with a test substance. The importance of occlusion for obtaining reliable and reproducible results became increasingly clear from the 1950's onwards. Various different types of patches have been brought forth with a view to obtaining occlusion and an adequate transfer of test substance to the skin: See for example U.S. Pat. No. 3,703,809, U.S. Pat. No. 3,894,531, U.S. Pat. No. 4,214,592, U.S. Pat. No. 4,158,359, U.S. Pat. No. 4,390,027, U.S. Pat. No. 4,450,844 and WO-A-86/01994. The term "patch" is construed in a very broad sense nowadays in the present context. In our specification and claims therefore the word "patch" designates the area carrying the test substance and applied to the skin. The most popular patches according to conventional technique are small cups of aluminum or plastic (Finn Chambers®, Epicon Oy, Finland, and Chemotechnique Diagnostic AB, Malmo, Sweden, respectively) or small aluminum disks provided with filter paper (Al-test, Holister Stier, USA). On these conventional patches, the test substance formulated in a suitable vehicle has been applied immediately before the testing. The vehicle most commonly employed has been petrolatum (vaseline), but in the case of some, problematic contact allergens (e.g. formaldehyde) it was preferred to employ patches of fabric or filter paper soaked with the test substance dissolved in a suitable solvent (e.g. water). WO-A-86/01994 and Br. J. Dermatol. 112 (1985) pp 63-8 are considered to have come forward with an entirely new generation of patches.

The technique is called "TRUE Test"; it employs a patch which is a thin, dry polymer film capable of absorbing moisture from a tested skin area when the patch is applied under occlusion against the skin The most preferred vehicles have been said to be those that will then form a gel In a patch according to the TRUE Test method, a homogeneous distribution of the test substance in the polymeric film has been achieved already in the manufacturing stage The TRUE Test is the first system capable of providing customers with high-quality patches comprising a guaranteed quantity of test substance.

Occlusive epicutaneous testing for demonstrating contact allergy is performed with pressure-sensitive adhesive strips on which one or more patches containing a test substance have been applied Such strips may thus carry as many as up to 25 patches, although in most cases the number of patches is less than 15. It is known that the strips can be wrapped in materials that are impermeable to air, moisture and light.

In the epicutaneous testing procedure, an allergenic substance in the form of a suitable formulation is applied to normal skin under occlusion for a predetermined period of time and in a correct manner. This will then, in contact allergy cases, produce an allergic eczema in the test area. Irritant substances give rise to irritative eczema reactions of a similar character (Manual of Contact Dermatitis: Fregert S., 2nd edition, Munksgaard, Copenhagen (1981), pp 71-6). The side of the patch facing away from the skin is impermeable to moisture, to thus provide the said occlusion.

As far as we know, prefabricated formaldehyde patches for use according to the conventional patch test have never been available commercially. Fairly satisfactory patches for use in the TRUE Test for the purpose of demonstrating formaldehyde allergy could be constructed by means of having formaldehyde or paraformaldehyde in the form of a cyclodextrin complex incorporated in a polymeric film (EP-A-252,044). It has been found, however, that alternative solutions are needed for tackling the problems relating to formaldehyde.

OBJECTS

One object of the invention is to provide patches and test strips which are stable on storage and are to be used diagnostically for determining whether or not an individual suffers from contact allergy to formaldehyde. Among further objects may be mentioned novel methods to be used for detecting contact allergy of the type as contemplated here.

THE INVENTION

One aspect of the invention is a test strip with at least one patch which is to specifically detect formaldehyde allergy. The special feature here is that on the said at least one patch the test substance is a reversible N-formaldehyde derivative of a carboxamide or -imide (so-called NH acid compounds). The term "reversible derivative" means that when water is present the test substance is capable of decomposing so as to form formaldehyde. A further characteristic feature is that the test substance is formulated in a dry vehicle which in the most preferred embodiment is capable of absorbing moisture from the tested skin area when the strip is being used. Upon contact with moisture from the skin, formaldehyde can be released from the derivative and then, if the person on whom the strip has been applied is sensitized to formaldehyde, a contact allergy reaction may result.

A minor aspect of the invention is the use of a reversible N-formaldehyde derivative of a carboxamide or -imide for producing a test composition which is to be used in accordance with the object of the present invention.

Reversible N-formaldehyde derivatives of the aforesaid type are well known to organic chemists Such derivatives can be produced easily in that an NH acid compound is reacted with formaldehyde, usually with recourse to heating. The solvent may be water, ethanol or dioxane Either equimolar amounts of formaldehyde and NH acid compound are employed in this synthesis, or formaldehyde is employed in excess over the NH acid compound. Formaldehyde has been employed in the form of either formalin or paraformaldehyde. In the scientific literature derivatives are described which are produced from ordinary amides, imides, carbamates, urea and derivatives thereof, hydantoins, barbiturates and uracil derivatives etc. A first step of the synthesis is conducive to N-hydroxymethylation (for example —CONH—CH$_2$OH and (—CO)$_2$N-CH$_2$OH), but further reactions are obtainable with amide or imide present (for example —CONH—CH$_2$—NHCO or (—CO)$_2$-N—CH$_2$—N(CO—)$_2$).

If the synthesis is carried out under suitable conditions and in the presence of a secondary amine it is possible to obtain final products which are so-called Mannich bases (for example —CONH—CH$_2$—N(CH$_3$)$_2$ in case dimethylamine is employed). Further derivatization of a previously introduced hydroxyl group may be carried out in separate synthesis steps, e.g. an esterification.

Reversible N-formaldehyde derivatives of drugs have been proposed as "prodrugs" with a view to obtaining an easy in vivo hydrolysis of the formaldehyde moiety that has been introduced. In the context of studies concerned with this type of use the hydrolysis of the N-formaldehyde derivatives has been subjected to careful examination; from the data published it can be seen how structure will affect the rate of hydrolysis (pH 7, blood). See Johansen M. & H. Bundgaard, Arch. Pharm. Chemi, Sci. Ed. 7 (1979) pp 175-92; Arch. Pharm. Chemi, Sci. Ed. 9 (1981) pp 40-2; Arch. Pharm. Chemi, Sci. Ed. 9 (1981) pp 43-54, and Bundgaard, H. & Johansen, M. Int. J. Pharm. 5 (1980) pp 67-77; J. Pharm. Sci. 69 (1980) pp 44-6; Arch. Pharm. Chemi, Sci. Ed. 8 (1980) pp 29-52.

The present invention while having profited from this knowledge about the reversible N-formaldehyde derivatives does not use those derivatives as "prodrugs" for medicines but, instead, as "prodrugs" for formaldehyde.

N-formaldehyde derivatives employed according to the invention should readily decompose in skin-secreted moisture to thus form formaldehyde. The other decomposition products as well as the N-formaldehyde derivative itself should give only a low or preferably no incidence of skin reactions of an allergic or irritative type. The substances thus should be inert and physiologically tolerable on the skin. The requirement that solely the one decomposition product which is formaldehyde itself is to produce a skin reaction makes it necessary to select N-formaldehyde derivatives of a type such that the course of their decomposition is well-defined, with direct formation of formaldehyde. The release of formaldehyde is pH-dependent and is determined by the structure of the derivatives. The decomposition rate of the derivatives will increase with rising pH. Since in our case a quick release is desired we have studied the structure vs decomposition interrelationship at pH 9 (that is, just below the pH value resulting in skin irritation). Our experimental results indicate that the interrelationship is substantially the same as at pH 7.4. Also, in so-called Guinea Pig Maximization tests we have determined the decomposition half-life values required in order to obtain an allergic reaction in formaldehyde sensitized guinea pigs. The results have shown unambiguously that the half-life period should be less than 7 hours (aqueous solution, pH 9.0, 0.1M HCO$_3^-$/CO$_3^{2-}$, concentration of derivative $8 \times 10^{-4}$M, 30° C.) This upper limit of the half-life should be understood as being only a general guideline. When the formaldehyde derivative is to be chosen a suitable study in an animal model should also be made, as a supplemental assessment means to thus establish that a given derivative will produce the intended reaction in formaldehyde sensitized individuals.

On the basis of our current knowledge the preferred substances are N-formaldehyde derivatized imides, e.g. cyclic imides such as phthalimide, succinimide, hydantoin etc. Mannich bases of carboxamides have been found to be hydrolytically unstable; for this reason they may well turn out to be superior formaldehyde release substances in the future. What is probably very essential for an N-formaldehyde derivative to be good for our purpose is that it has to be soluble in water, possibly also with the additional requirement that its dissolution proceeds quickly.

The vehicle

In order for an N-formaldehyde derivate of an NH acid compound to undergo decomposition it is necessary that water is present. This is why the technique of WO-A-86/01994 is eminently suitable in the context of our invention. It is preferred, thus, that the N-formaldehyde derivate be formulated in a dry film (=vehicle, usually 0.25 mm or thinner) comprising as a film-forming polymer. A polymer which when used in the test is able to absorb moisture. Of course this will not rule out other ways of formulating the derivative. Thus for instance also vaseline is quite conceivably a useful medium, the hydrolysis (decomposition) in this case taking place at the skin-vaseline interface.

To fulfill the moisture absorption requirement the polymer has to comprise a multitude of polar structure; and moreover it has to be a good film former. The suitability of a given polymer can easily be assessed by means of simple preliminary tests. Information about various properties reflecting the suitability of a polymer is also available from producers and textbooks (see for example Encyclopedia of Polymer Science and Technology: Plastics, Rubbers, Resins, Fibers; Jon Wiley & Sons Inc., Vol. 6 pp 778-9 (1967)). Examples of polar structures are ester groups, ether groups, amide groups etc. The degree of hydrophobicity (lipophilicity/hydrophilicity) is determined, broadly, by the number (density) of polar groups and the polarity thereof. An optimum choice of the polymer will depend on the N-formaldehyde derivative, the solvent (if any) employed for formulation, and the substrate to which the film is to be affixed (film carrier).

When the vehicle is selected important points to be taken into consideration are that the vehicle has to be acceptable pharmaceutically and to be non-irritant to the skin, inert to the film carrier etc.

Manufacture of a test patch on which an N-formaldehyde derivative has been formulated in a film (according to the TRUE Test)

In order to secure good test results with the final product the following two conditions are of critical importance: (1) The N-formaldehyde derivative should be formulated without the use of water during that process: The presence of water is conducive to gradual hydrolysis, and in that case the content of test substance in the patch cannot be guaranteed. (2) The N-formaldehyde derivative is to be distributed uniformly in the film-forming material; this material in turn is to be spread out as a layer of uniform thickness on a so-called film carrier. As regards the film carrier to be chosen see WO-A-86/01994.

Earlier patent publications dealing with the TRUE Test emphasize that the film-forming polymer together with a volatile liquid should be able to give a gel or a coalescent emulsion. Water in particular is mentioned. This requirement is set up for reasons of formulation technique.

The manufacturing process now used for test strips according to WO-A-86/01994 spreading of the gel or emulsion must be feasible in such a manner that thin layers thereof are obtained, these layers being then allowed to dry to thus form a supple film. In view of the fact that the N-formaldehyde derivatives contemplated here are so sensitive to hydrolysis it is recommendable, in the context of this invention, to employ film-forming polymers which will produce the desired gel or emulsion when they are combined with non-aqueous solvents, preferably aprotic. It may be determined by means of some simple preliminary tests whether or not a given polymer is suitable for use in combination with a given solvent.

In the method which is currently the best known for producing the film, the N-formaldehyde derivative is added to a film-forming polymer which is lipophilic in character, for example polyvinyl pyrrolidone, dissolved or gelled in an aprotic solvent which is volatile. This may be done by dispersing or emulsifying the N-formaldehyde derivative homogeneously in a finely divided state into the gel. Next, the film carrier is coated with a gel layer of uniform in thickness which is allowed to dry, the film sheet thus obtained being then cut up into a suitable number of patches, which are preferably equal in shape and size (area). The thickness of the dried film as obtained may vary, depending on the amount of gel that has been applied. The area of the patches is usually one within the range of 0.2 to 4 cm$^2$. In the film the amount of N-formaldehyde derivative per unit area will depend on the particular derivative employed, the vehicle and any buffer systems that may optionally have been added. Note in this context that the hydrolysis rate of N-formaldehyde derivatives is pH-dependent. For this reason it is recommendable that dry buffer components are dispersed into the aforesaid gel so that then the moisture secreted is buffered to a pH which is physiologically tolerable on the skin and is acceptable in respect of formaldehyde release. Depending on the derivative employed, the pH may be selected within the range of from 4 to 10. By means of such buffering the release of formaldehyde is no longer dependent on the pH of the moisture secreted by the person tested. Suitable buffer systems are $HCO_3^-/CO_3^{2-}$, $HPO_4^{2-}/PO_4^{3-}$, $H_2PO_4^-/HPO_4^{2-}$, $AcOH/AcO^-$ etc.

The patches are then placed on sheets of pressure-sensitive adhesive material (the film side being made to face away from the sheet) which provide a projecting margin of at least 1 cm all around each patch. To facilitate the testing procedure, several different contact allergens may be placed on one sheet. It is essential, for the sake of obtaining a guaranteed content of test substance in the patches, that they be packaged in a manner as known in TRUE Test contexts, the wrapping material being in principle impervious to moisture, light and air. In the case of the N-formaldehyde derivates employed according to the invention, as well as in case of several other test substances, it is possible to still further improve storage stability properties by additionally enclosing desiccants in the package.

Testing Procedure

This procedure is carried out in a known per se manner with a patch or test strip of the type described above. One or more patches (test strips) are attached to the patient's skin in a manner such that the vehicle (film) will contact the skin area to be tested, whereupon the strip is sealingly pressed against the skin into a fixed position. Removal of the strip (patches) will normally take place after some 40-50 hours; reading of the result will then follow after a further 20-30 hours.

The invention is defined in the attached claims which form part of the present specification.

EXAMPLE 1

Determining the decomposition half-life of a variety of N-hydroxymethyl derivatives of amides and imides Equipment: Spectroscopic measurements were perfomed with a Zeiss PMQ II spectrophotometer. The pH was measured with a Radiometer PMM-83 instrument.

Materials: N-(hydroxymetyl)-benzamide (Hellman, H, Angew. Chem. 69 (1957), 470), N-(hydroxymethyl)-nicotinamide (Chechelska, B. & Urbanski, T., Roczniki Chem. 27, 396-409), N-(hydroxymethyl)-phthalimide (Buch, S. R., J. Am. Chem. Soc. 69 (1947) 254- ), N-(hydroxymethyl)-hydantoin (Konishiroku Photo Industr. Co. Ltd. Japan 6882 ('58) Aug. 20, Chemical Abstracts 54, 135h), N-hydroxymethyl succinimide (Vail, S. L. & Pierce, A. G., J. Org. Chem. 37 (1972) 393-), and the Mannich bases N-dimethylaminomethyl nicotinamide (Singh, G. et al., Indian J. Pharm. 30 (1968) 231-3) and N-dimethylaminomethyl succinimide (Boehme, H. et al., Ann. Chem. 664 (1963) 130-40) were produced in a known manner.

Kinetics measurement: Decomposition was allowed to proceed in buffers of carbonate (0.1M, pH 9.03), phosphate (0.1M, pH 6.0, 7.12, 7.20, and 0.05M, pH 6.15) and acetate (0.05M and 0.1M, pH 4.0), at a temperature of 30° C. The initial concentration of the N-formaldehyde derivatives was $0.1-1\times10^{-3}$M and that of the Mannich bases was $2\times10^{-4}$M Reactions were monitored by means of measuring the release of formaldehyde in accordance with the colorimetric method described below. For fast reactions, recourse was had to the below alternative "trapping" method. On appropriately timed sampling occasions samples of 1,000 /$\mu$l were taken; these were diluted with water to 10.00 ml, and then 500 /$\mu$l of each dilution were analyzed. The pseudo first order rate constants were calculated on the basis of linear plots of $\log(A-A_t)$ against time, where A and $A_t$ are the absorbance read (625 nm) at infinity and at time t respectively. For results, see below.

Determinations: Release of formaldehyde was determined as according to Johansen, M. & Bundgaard, H. (Arch. Pharm. Chemi., Sci. Ed. 7 (1979) pp 178-). 500 $\mu$l of test solution (about $8\times10^{-4}$M) were mixed with 400 /$\mu$l of 0.1M acetate buffer (pH 4.0) and 100 $\mu$l of 0.5% aqueous solution of 3-methylbenzothiazole-2-one hydrazone hydrochloride. After 30 minutes at room temperature 500 /$\mu$l of an aqueous solution were added which contained 0.25% of Fe(III+) chloride hexahydrate. After a further period of 10 minutes 1 500 /$\mu$l of water were added, and the absorbance of the mixture was read at 625 nm against a blank containing the reagents. The formaldehyde concentration in the test solution was then calculated with the aid of a standard curve for formaldehyde.

"Trapping" of formaldehyde: At pH 9.0 the decompositon rates of the N-hydroxymethyl derivatives of succinimide, phthalimide and hydantoin and the Mannich bases (N,N-dimethylaminomethyl succinimide and N,N-dimethylaminomethyl nicotinamide) were too high to be determinable colorimetrically. However the reaction rate could be monitored spectrophotometrically in that the formaldehyde that had formed was trapped with semicarbazide and the increase of absorbance for semicarbazone (235) was measured. Semicarbazide hydrochloride ($10^{-2}$M) was therefore included in the buffer in which decompositon was to take place.

TABLE 1

Results
Observed pseudo first order rate constants ($c_{obs}$) of formaldehyde
formation from various N-formaldehyde derivatives in buffer solutions

| Buffer solution | N-(hydroxymethyl) benzamide ($h^{-1}$) | N-(hydroxymethyl) nicotinamide ($h^{-1}$) | N-(hydroxymethyl) succinimide ($h^{-1}$) | N-(hydroxymethyl) phthalimide ($h^{-1}$) | N-(hydroxymethyl) hydantoin ($h^{-1}$) |
|---|---|---|---|---|---|
| 0.1M carbonate pH 9.03 | 0.11 | 0.77 | n.p.d. | n.p.d. | — |
| 0.1M phosphate pH 7.36 | n.d. | n.d. | 12.4 1) | n.p.d. | — |
| 0.1M phosphate pH 7.12 | — | — | 16.5 1) | | 16.5 1) |
| 0.1M phosphate pH 6.00 | n.d. | n.d. | 3.2 | | — |
| 0.1M acetate pH 4.00 | n.d. | n.d. | 0.02 | | — |
| | N,N-dimethyl aminomethyl succinimide | N,N-dimethyl aminomethyl succinimide | | | |
| 0.05M acetate pH 4.00 | n.p.d. | n.p.d. | | | |
| 0.05M phosphate pH 6.15 | n.p.d. | — | | | |

1) Determined at room temperature with semicarbazide in the reaction mixture ("trapping").
n.d. = No detectable release of formaldehyde
n.p.d. = Not possible to determine because the rate at which formaldehyde was being released was too high.

Earlier investigations into the decomposition of compounds as contemplated here have shown that the rate is independent of the buffer concentrations (0.02–0.2M) employed for maintaining a constant pH. For the pH range comprising the values set forth in Table 1 it has been shown earlier that the pseudo first order rate constants observed are directly proportional to the hydroxide ion concentration (Johansen, M. & Bundgaard, H., Arch. Pharm. Chemi, Sci. Ed. 7(1979) 178-).

$$c_{obs} = c \times (OH^-)$$

Using this equation it is possible to calculate the rate constant c and half-life at pH 9 (temp. 30° C.) of a given N-formaldehyde derivative on the basis of a measured $c_{obs}$ value.

In dilute solutions (about $1 \times 10^{-3}$M) the formation of amide/imide was favoured. With increasing initial concentrations of N-hydroxymethyl derivative it was observed that fomaldehyde was not formed in stoichiometric amounts. On the basis of the pseudo first order rate constants determined, the half-lives of the derivatives examined have been calculated as being approximately the following: Benzamide derivative 6.3 hours; nicotinamide derivative 0.7 hour: succinimide derivative 0.03 minute; phthalimide derivative less than 0.03 minute; hydantoin derivative 0.03 hour; and the two Mannich bases studied, less than 0.03 minute.

EXAMPLE 2

Guinea Pig Maximization test with N-hydroxymethyl derivative of benzamide, nicotinamide, phthalimide, succinimide and hydantoin Testing procedure: The Guinea Pig Maximization test was performed in a known manner (Magnusson, B. & Kligman, A. M., J. Invest. Dermatol. 53 (1969) pp 268-76; Wahlberg, J. E. & Boman, A., Curr. Probl. Derm. 14 (1985) pp 59–106); and Andersen, K. E. et al, Acta Derm. Venereol. 65 (1985) pp 472-8).

Manufacture of patches

Patches with N-hydroxymethyl derivatives were produced. A detailed description will follow for the case of the succinimide derivative. Formulation of the other derivatives was analogous. 20.00 g of N-hydroxymethyl succinimide were suspended in 68.00 g of methylene chloride (1 min, Ultra-torrax 9 500 rpm). Then followed an addition of dry sodium bicarbonate (0.400 g, finely divided) and dry sodium carbonate (0.060 g, finely divided). Finally 7.000 g of polyvinyl pyrrolidone (Polyvidone, GAF Corporation) were added, with stirring at a rate of 300 rpm. Thereafter the stirring rate was set at 50 rpm for 1 hour. The mass which had a gel-type consistency was then spread as a film of uniform thickness (70 μm) on a polyester sheet (Mylar Type D, Dupont) which had a thickness (70 /μm) on a polyester sheet (Mylar Type D, Dupont) which had a thickness of 75 /μm. Upon drying a thin supple film was obtained which had a thickness of about 30 /μm. The film coated sheet was then cut up into square patches, 0.79 cm² each, which were placed onto a pressure-sensitive adhesive sheet, with an at least 1 cm free margin of that sheet being left around each patch. Analysis of the patches obtained showed that they contained 0.08 mg/cm² formaldehyde in the form of N-hydroxymethyl succinimide. The sheets (test strips) were then individually wrapped into laminated aluminium foils so as to form packages impervious to light, air and moisture, and were stored at different temperatures for different lengths of time. Thereafter they were analyzed in respect of their residual content of formaldehyde in the form of N-hydroxymethyl succinimide. Results:

| Temperature | Storage time, weeks | | | |
|---|---|---|---|---|
| | 4 | 7 | 14 | 25 |
| 8° C. | 102% | 110% | 97% | 112% |
| 25° C. | 98% | 119% | 93% | 75% |
| 40° C. | 46% | 42% | 31% | 17% |

Similar tests were made with other concentrations of N-hydroxymethyl succinimide. The tests showed stability to be satisfactory for storage at 8° C. during a period of up to 9 months. Also, the tests showed storage stability to be independent of the test substance concentration on the patch.

By means of varying the amount of N-hydroxymethyl succinimide, and by replacing this substance with the N-hydroxymethyl derivatives of benzamide, nicotinamide, phthalimide and hydantoin, patches were produced which carried the belowlisted concentrations with reference to formaldehyde. All the patches were of 0.79 cm² size.

| N-hydroxymethyl derivative of: | Conc., mg/cm², with ref. to formaldehyde |
| --- | --- |
| benzamide | 2.07 and 0.80 |
| nicotinamide | 0.30 and 0.62 |
| phthalimide | 0.43 and 0.84 |
| hydantoin | 3.09 |
| succinimide | 0.5 and 0.12 |

The patches were then used in the Guinea Pig Maximization test. Patches employed for comparison were (i) Finn Chambers ® with 1% formaldehyde in water (v/v) (30 /µl on two Finn Chamber ® filters in one Finn Chamber ® gave 0.78 mg/cm²), and (ii) formulations according to the TRUE Test of benzamide (6.80 mg/cm²), nicotinamide (7.7 mg/cm²), phthalimide (3.60 mg/cm²), hydantoin (3.60 mg/cm²) and succinimide (0.5 mg/cm²). Two groups of guinea pigs were employed in each test series: (a) 9 non-sensitized animals and (b) 20 formaldehyde sensitized animals. The test preparations were applied under occlusion against the flanks of the animals where all hair had been carefully removed on 5×5 cm skin areas. After 24 hours the preparations were removed and readings of the test results were taken twice after a further 24 and 48 hours. The aforesaid skin areas were subjected to hair cutting and shaving also 2 hours before each reading. The responses as thus read off was assigned a score according to the following system of graduation: 0=no visible reaction; 1=erythemas discrete and in the form of spots; 2=moderate or coherent erythema; 3=severe erythema and swelling. The results obtained may be summarized as follows:

N-hydroxymethyl benzamide did not give any contact-allergic reaction at any of the concentrations tested. Since the reaction with the formaldehyde solution is positive the negative result obtained with N-hydroxymethyl benzamide must be due to the slow release of formaldehyde ($t_{\frac{1}{2}}$=6.3 hours at pH 9). It is interesting to note that the response is negative despite the fact that the formaldehyde concentration as the N-hydroxymethyl derivative is 3 times higher than that in the Finn Chambers ® employed. With the N-hydroxymethyl nicotinamide formulations, positive reactions were obtained only at the higher concentration (0.62 mg/cm²)

The allergic reaction obtained with N-hydroxymethyl phthalimide was weaker than that obtained with N-hydroxymethyl nicotinamide even though the phthalimide derivative decomposes much more quickly at pH 9 (30° C.) as compared to the nicotinamide derivative ($t_{\frac{1}{2}}$ = <<0.03 min. and 0.7 hr. respectively). It is therefore not possible to establish a linear correlation between the response in vivo and the decomposition rate half life in vitro. Possibly this is due to different solubility and diffusion properties.

In the case of the phthalimide and hydantoin derivatives, there were some indications that the control group animals were actually sensitized; this was disturbing for an adequate interpretation of the experimental results. Such disturbance was found to occur when the hydantoin derivative was tested, and we therefore could not obtain unambiguous results with this derivative.

With N-hydroxymethyl succinimide, test results were obtained which clearly agreed with those obtained when Finn Chambers ® with formaldehyde were used.

To sum up, it can be established with respect to the N-hydroxymethyl derivatives studied that there is a mutual relationship between their decompositon rate at pH 9 and their ability to produce an allergic reaction in formaldehyde sensitized guinea pigs when they are used as test substances in occlusive contact allergy testing procedures. It turned out that the very best of these substances was undoubtedly the compound N-hydroxymethyl succinimide.

We claim:

1. A test strip comprising at least one patch thereon containing a test substance which is suitable for use in occlusive epicutaneous testing in order to detect contact allergy to formaldehyde, wherein the test substance on at least one of said at least one patch is a reversible N-formaldehyde derivative of succinimide, said derivative
   (i) having been formulated in a dry vehicle together with a buffer substance that provides a pH-value within 4–10,
   (ii) decomposing in an aqueous solution of pH 9 containing 0.1M of $HCO_3^-/CO_3^{2-}$, and a concentration of test substance of $8 \times 10^{-4}$M at a half life rate of less than 7 hours, and
   (iii) giving substantially no incidence of skin reactions of an allergic or irritative type.

2. A test strip according to claim 1 wherein the vehicle is capable of absorbing moisture from a tested skin area when the strip is in use.

3. A test strip according to claim 1 wherein the vehicle is a polymeric film which covers the patch and is capable of absorbing moisture secreted from a tested skin area, thus forming a gel.

* * * * *